United States Patent
Hwan et al.

[11] Patent Number: 5,811,597
[45] Date of Patent: Sep. 22, 1998

[54] METHOD FOR THE MANUFACTURE OF METHYL TERTIARY BUTYL ETHER FROM TERTIARY BUTYL ALCOHOL AND METHANOL

[75] Inventors: Rei-Yu Judy Hwan, Sugarland; Mark Elliott Taylor, Orange; John Frederick Knifton, Austin; Melvin Ernest Stockton, Georgetown; John Ronald Sanderson, Leander, all of Tex.

[73] Assignee: Huntsman Specialty Chemicals Corp., Austin, Tex.

[21] Appl. No.: 703,269

[22] Filed: Aug. 26, 1996

[51] Int. Cl.⁶ .......................... C07C 41/06; C07C 41/09; C07C 41/34; B01D 3/00

[52] U.S. Cl. .................. 568/697; 203/29; 203/45; 203/46; 203/73; 568/698; 568/699

[58] Field of Search .................. 203/29, DIG. 6, 203/43, 45, 44, 46, 71, 73, DIG. 9, DIG. 23, 18, 14; 568/697, 699, 698

[56] References Cited

U.S. PATENT DOCUMENTS

| | | | |
|---|---|---|---|
| 4,544,776 | 10/1985 | Ostenburg et al. | 203/71 |
| 5,157,163 | 10/1992 | Smith et al. | 203/92 |
| 5,243,091 | 9/1993 | Kruse et al. | 568/697 |
| 5,336,841 | 8/1994 | Adams | 203/DIG. 6 |
| 5,354,912 | 10/1994 | Hwan et al. | 568/697 |
| 5,563,301 | 10/1996 | Preston et al. | 568/698 |
| 5,565,068 | 10/1996 | Parker et al. | 203/78 |
| 5,659,091 | 8/1997 | Peters et al. | 568/697 |

*Primary Examiner*—Virginia Manoharan
*Attorney, Agent, or Firm*—Russell R. Stolle; Carl G. Ries

[57] ABSTRACT

Methyl tertiary butyl ether is prepared from contaminated TBA by reactively distilling the contaminated TBA in a reactive distillation column to provide a lower boiling isobutylene fraction and a higher boiling aqueous TBA fraction, by distilling the higher boiling aqueous TBA fraction to provide a lower boiling TBA fraction, by charging the lower boiling isobutylene fraction, the lower boiling tertiary butyl alcohol fraction and methanol to an etherification reactor to form an etherification reaction product, by distilling the etherification reaction product to provide a lower boiling fraction containing isobutylene, methanol and methyl tertiary butyl ether by charging the lower boiling fraction to a finishing reactor to react the isobutylene and methanol contained therein to from additional MTBE and by recovering MTBE from the etherification reaction product and the isobutylene conversion product.

8 Claims, 1 Drawing Sheet

FIG. 1

METHOD FOR THE MANUFACTURE OF METHYL TERTIARY BUTYL ETHER FROM TERTIARY BUTYL ALCOHOL AND METHANOL

BACKGROUND OF THE INVENTION

1. Technical Field of the Invention

This invention relates to a process for the manufacture of methyl tertiary butyl ether (MTBE) from tertiary butyl alcohol (TBA) and methanol (MeOH). More particularly, this invention relates to a process for the manufacture of MTBE from peroxides-contaminated TBA and MeOH wherein the peroxides-contaminated TBA is preliminarily charged to a reactive distillation column containing a bed of a TBA dehydration catalyst to decompose the peroxide contaminants and to dehydrate a portion of the TBA to form isobutylene (IBTE) and wherein isobutylene and TBA from the reactive distillation column are reacted with methanol to form MTBE.

Still more particularly, this invention relates to a process wherein TBA contaminated with oxygen-containing impurities such as peroxides, formates, etc., is charged to a reactive distillation column containing a bed of a TBA dehydration catalyst to decompose the oxygen-containing contaminants, to dehydrate a portion of the TBA to form isobutylene (IBTE) and water, to separate the dehydration reaction products in the reactive distillation column into a lower boiling isobutylene fraction and a higher boiling aqueous TBA fraction, to the distillation of the higher boiling aqueous TBA fraction in a first distillation column to form a first lower boiling TBA fraction and a first higher boiling water fraction, to the reaction of the lower boiling isobutylene fraction and the first lower boiling TBA fraction with methanol in an etherification reactor to form an etherification reaction product comprising unreacted methanol, unreacted TBA, water, isobutylene (IBTE) and MTBE, to the distillation of the etherification reaction product in a second distillation column to provide a second lower boiling isobutylene fraction comprising isobutylene, methanol and methyl tertiary butyl ether and a second higher boiling tertiary butyl alcohol distillation fraction comprising methanol, tertiary butyl alcohol and water, and to the reaction of isobutylene from the second lower boiling isobutylene fraction with methanol in the lower boiling isobutylene fraction in a finishing reactor to form an isobutylene conversion product comprising methyl tertiary butyl ether, unreacted methanol, unreacted isobutylene and tertiary butyl alcohol.

2. Prior Art

The preparation of methyl tert-butyl ether from methyl and tert-butyl alcohols is discussed in S. V. Rozhkov et al., *Prevrashch Uglevodorodov, Kislotno-Osnovn. Geterogennykh Katal. Tezisy Dokl., Vses. Konf.*, 1977, 150 (C. A. 92:58165y). Here the TBA and methanol undergo etherification over KU-2 strongly acidic sulfopolystyrene cation-exchangers under mild conditions. This reference contains data on basic parameters of such a process.

In U.S. Pat. No. 4,144,138 (1979) to Rao et al., there is disclosed a method for manufacture of methyl tertiary butyl ether from tertiary butyl alcohol and methanol and for resolving the etherification reaction effluent by azeotropic distillation.

Kruse et al. U.S. Pat. No. 5,243,091 discloses a method for the preparation of methyl tertiary butyl alcohol wherein peroxides-contaminated tertiary butyl alcohol is passed through a peroxides-decomposition reactor to decompose the peroxides after which the peroxides-free tertiary butyl alcohol is catalytically reacted with methanol to form a reaction product that is separated into a lower boiling isobutylene distillation fraction comprising isobutylene, methanol and methyl tertiary butyl ether and a higher boiling distillation fraction comprising methanol, tertiary butyl alcohol and water, wherein the lower boiling isobutylene distillation fraction and a first recycle isobutylene fraction are reacted to form an isobutylene conversion product that is charged, together with recycle isobutylene to a methanol extraction zone and countercurrently contacted with water to provide an overhead raffinate comprising aqueous isobutylene, and wherein the isobutylene is recovered and recycled.

Gupta U.S. Pat. No. 5,292,964 discloses a method for the preparation of methyl tertiary butyl alcohol wherein a mixture of methanol and tertiary butyl alcohol is catalytically reacted to form a reaction product containing the water of etherification and at least one mol of methanol per two moles of methyl tertiary butyl ether, wherein the reaction product is fractionated to separate a lower boiling methanol and methyl tertiary butyl ether fraction from the water and tertiary butyl alcohol and wherein the methanol in the lower boiling distillation fraction is reacted with isobutylene to form additional methyl tertiary butyl ether.

Gupta states that it is essential to provide a reaction product containing at least one mol of methanol per two moles of methyl tertiary butyl ether, so that water is separable from the methyl tertiary butyl ether in the fractionating column to provide a lower boiling distillation fraction substantially free from water.

Grane et al. U.S. Pat. No. 4,296,262 is representative of patents directed to the manufacture and recovery of tertiary butyl alcohol by the thermal decomposition of tertiary butyl hydroperoxide.

Smith U.S. Pat. No. 4,215,011 discloses a reactive distillation column having both a catalytic function and a distillation function that is useful, for example, in the polymerization of butene.

In Smith U.S. Pat. No. 4,232,177, a method for conducting chemical reactions in a reactive distillation column is disclosed wherein a reaction mixture is fed to a reactive distillation column and contacted with a fixed bed of catalytic packing concurrently to carry out the reaction and to fractionate the reaction mixture.

Various types of catalytic packing that can be used in a reactive distillation column are disclosed in Smith U.S. Pat. No. 4,443,559.

Smith U.S. Pat. No. 5,118,873 discloses a process wherein isobutylene and methanol are reacted in the presence of an acid cation exchange resin to form MTBE and concurrently fractionated to provide an overhead fraction comprising unreacted isobutylene and unreacted methanol and a bottoms fraction comprising methyl tertiary butyl ether and contaminants.

Matouq et al. discuss a "Combined Process for Production of Methyl Tert.-Butyl Ether from Tert.-Butyl Alcohol and Methanol" at *Journal of Chemical Engineering of Japan*, Vol. 27, No. 3, 1994, pp. 301–306.

Another discussion of the formation of methyl tertiary butyl ether is found in a paper entitled "Why Methyl Tert.-Butyl Ether Production by Reactive Distillation May Yield Multiple Solutions," *Ind. Eng. Chem. Res.* 1995, Vol. 34, pp. 987–991.

A study of the dehydration of tertiary butyl alcohol is disclosed in an article by Ohtsuka et al. entitled "Studies of the Acidity and Ionic Conductivity of Silica-Supported Heteropoly Compounds. I. The Dehydration of t-Butyl Alcohol over Heteropoly Compound Catalysts," *Bull. Chem. Soc. Jpn.*, Vol. 62, 3195–3201 (1989).

The manufacture of isobutylene by the dehydration of tertiary butyl alcohol is also discussed by Abraham et al. in a paper entitled "Make Isobutylene from TBA," *Hydrocarbon Processing*, February 1992, pp. 51–54.

Another paper discussing the dehydration of tertiary olefins by Kantam et al., entitled "Montmorillonite Catalyzed Dehydration of Tertiary Alcohols to Olefins," is found in the *Tetrahedron Letters*, Vol. 34, No. 7, pp. 1185–1186 (1993).

SUMMARY OF THE INVENTION

This invention relates to a process comprising the steps of:

a) charging TBA contaminated with oxygen-containing impurities such as peroxides and formates, to a reactive distillation column containing a bed of a TBA dehydration catalyst to decompose the oxygen-containing contaminants, to dehydrate a portion of the TBA to form isobutylene (IBTE) and water, and to separate the dehydration reaction products in the reactive distillation column into a lower boiling isobutylene fraction and a higher boiling aqueous TBA fraction, b) charging the higher boiling aqueous TBA fraction to a first distillation column and fractionating it therein to form a first lower boiling TBA fraction and a first higher boiling water fraction, c) charging the lower boiling isobutylene fraction, the first lower boiling TBA fraction and methanol to an etherification reactor and reacting them therein to form an etherification reaction product comprising unreacted methanol, unreacted TBA, water, isobutylene (IBTE) and MTBE, d) charging the etherification reaction product to a second distillation column and fractionating it therein to provide a second lower boiling isobutylene fraction comprising isobutylene, methanol and methyl tertiary butyl ether and a second higher boiling aqueous distillation fraction comprising methanol, tertiary butyl alcohol and water, e) charging the second lower boiling isobutylene fraction and an isobutylene conversion product to a water-washing tower for countercurrent contact with water to form a raffinate comprising MTBE, isobutylene and water and an extract comprising MTBE, methanol and water, f) charging the raffinate to a third distillation zone and separating it therein into a third higher boiling MTBE product fraction and a third water fraction and a third isobutylene fraction, g) charging the third isobutylene fraction and methanol to a finishing reactor and reacting the isobutylene with methanol to form the said isobutylene conversion product comprising methyl tertiary butyl ether, unreacted methanol, unreacted isobutylene and tertiary butyl alcohol, and h) recovering MTBE from the etherification reaction product and the isobutylene conversion product.

A further embodiment of the present invention includes the additional steps of:

i) charging the second higher boiling aqueous distillation fraction from the second distillation column and the extract from the water-washing tower to a fourth distillation column and separating them therein into a fourth lower boiling MTBE fraction and a fourth higher boiling aqueous methanol fraction, j) recycling the fourth lower boiling MTBE fraction to the water washing tower, and k) separating methanol from the water in the fourth higher boiling aqueous methanol fraction and recycling the separated methanol to the etherification reactor.

DESCRIPTION OF PREFERRED EMBODIMENTS

In accordance with a preferred embodiment of the present invention, a method for the continuous preparation of methyl tertiary butyl ether (MTBE) from tertiary butyl alcohol (TBA) and methanol (MeOH) is provided comprising the steps of:

a) continuously charging a tertiary butyl alcohol feedstock contaminated with peroxides and formates to a reactive distillation reactor containing a bed of a tertiary butyl alcohol dehydration catalyst, dehydrating tertiary butyl alcohol therein to form isobutylene and water and substantially completely decomposing the peroxide and formate contaminants therein to form a substantially peroxides and formates free tertiary butyl alcohol reaction product comprising unreacted tertiary butyl alcohol, isobutylene and water, and fractionating said tertiary butyl alcohol reaction product therein to provide a lower boiling isobutylene fraction and a higher boiling aqueous TBA fraction, b) continuously charging the higher boiling aqueous TBA fraction to a first distillation column and fractionating it therein to form a first lower boiling TBA fraction and a first higher boiling water fraction, c) continuously charging a reaction feed mixture comprising methanol, the lower boiling isobutylene fraction and the first higher boiling TBA fraction to an etherification reactor containing a bed of a TBA/MeOH etherification catalyst and reacting said reaction feed mixture therein to form an etherification reaction product comprising unreacted methanol, unreacted tertiary butyl alcohol, water, isobutylene and methyl tertiary butyl ether, d) continuously charging the etherification reaction product to a second distillation column and fractionating it therein to provide a second lower boiling isobutylene distillation fraction comprising isobutylene, methanol and methyl tertiary butyl ether and a second higher boiling tertiary butyl alcohol distillation fraction comprising methanol, tertiary butyl alcohol and water, e) charging the second lower boiling isobutylene fraction and an isobutylene conversion product to a water-washing tower for countercurrent contact with water to form a raffinate comprising MTBE, isobutylene and water and an extract comprising MTBE, methanol and water, f) charging the raffinate to a third distillation zone and separating it therein into a third higher boiling MTBE product fraction and a third water fraction and a third isobutylene fraction, and g) continuously charging the third isobutylene fraction and methanol to an isobutylene finishing reactor containing a solid resin etherification catalyst and reacting the isobutylene with methanol therein to form said isobutylene conversion product comprising methyl tertiary butyl ether, unreacted methanol, unreacted isobutylene tertiary butyl alcohol and water.

A further embodiment of the present invention includes the additional steps of:

h) charging the second higher boiling methanol distillation fraction from the second distillation column and the extract from the water-washing tower to a fourth distillation column and separating them therein into a fourth lower boiling MTBE fraction and a fourth higher boiling aqueous methanol fraction, i) recycling the fourth lower boiling MTBE fraction to the water washing tower, and j) separating methanol from the water in the fourth aqueous methanol fraction and recycling the separated methanol to the etherification reactor.

DETAILED DESCRIPTION OF THE PRESENT INVENTION

Dehydration of Tertiary Butyl Alcohol

It is known to prepare tertiary butyl alcohol by the thermal or catalytic decomposition of tertiary butyl hydroperoxide. It is also known to prepare tertiary butyl alcohol by the catalytic reaction of tertiary butyl hydroperoxide with propylene to form propylene oxide and tertiary butyl alcohol. The tertiary butyl alcohol feedstock derived from tertiary butyl hydroperoxide in this manner will contain peroxide contaminants. A typical feedstock prepared in this fashion will contain from about 95 to 99 wt. % of tertiary butyl alcohol and less than about 2.0 wt. % of peroxide contaminants such as tertiary butyl hydroperoxide, ditertiary butyl peroxide, allyl tertiary butyl peroxide, etc. and will also contain formate contaminants such as methyl formate and formic acid, etc.

The Reactive Distillation Column

In accordance with the IBTE manufacture and purification method of the present invention, a tertiary butyl alcohol feedstock contaminated with peroxide contaminants and formate contaminants is dehydrated to form isobutylene and water while decomposing the peroxide and formate contaminants by charging the contaminated tertiary butyl alcohol feedstock to a reactive distillation column which contains a bed of a tertiary butyl alcohol dehydration catalyst. A wide variety of tertiary butyl alcohol dehydration catalysts can be used for this purpose, such as HF treated beta zeolite catalyst, a HF treated clay catalyst, etc. A preferred catalyst is a HF treated beta zeolite catalyst.

Zeolites as disclosed in Japanese Patent 0007432 and aluminosilicate zeolites as disclosed in Chang et al. U.S. Pat. No. 4,058,576 may also be used.

The reaction conditions to be utilized when dehydrating tertiary butyl alcohol in the presence of a tertiary butyl alcohol dehydration catalyst include a reaction temperature of about 180° to about 220° C., and a pressure of about 0 to about 500 psia, a distillation top temperature of about 25° to about 60° C., and a distillation bottom temperature of about 70° to about 205° C.

The reactive distillation column to be used in accordance with the present invention is a reactive distillation column of the type disclosed in the Smith patents referenced above.

The tertiary butyl alcohol feedstock is charged to the reactive distillation column under reaction conditions, as described above, where it is dehydrated to form a reaction product comprising unreacted tertiary butyl alcohol, isobutylene, and water. The lower boiling components of the dehydration product comprising isobutylene will flow upwardly through the reactive distillation column where the IBTE is recovered as a lower boiling isobutylene distillation fraction. The higher boiling components of the dehydration product, including water and tertiary butyl alcohol will flow downwardly through the reactive distillation column where a higher boiling aqueous tertiary butyl alcohol fraction is recovered.

The tertiary butyl alcohol feedstock will normally contain from about 90 to about 98 wt. % of tertiary butyl alcohol and impurities including from about 0.05 to about 2 wt. % of water, from about 0.1 to about 2 wt. % of methanol and minor amounts (e.g., less than 1 wt. % each) of contaminants including contaminants such as isobutylene, diisobutylene, methyl tertiary butyl ether, tertiary butyl hydroperoxide, ditertiary butyl peroxide, allyl tertiary butyl hydroperoxide, methyl formate, formic acid, acetone, etc.

The Etherification Reaction Catalyst

In accordance with the MTBE manufacture and purification method of the present invention, an etherification reactor containing a bed of etherification catalyst is utilized. A preferred catalyst is a sulfonic acid resin etherification catalyst such as a sulfonated polystyrene resin cross-linked with divinyl benzene.

Any suitable solid resin etherification catalyst may be used for this purpose, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Dowex M-31", "Dowex M-32", "Nalcite HCR", "Amberlyst A-15", "Amberlyst A-16", etc. The use of catalysts of this nature is disclosed, for example, in Rao U.S. Pat. No. 4,144,138.

A variety of supported phosphorus acid-type catalysts can be used, such as Kieselguhr impregnated with phosphoric acid as disclosed in Frolich U.S. Pat. No. 2,282,469, titania impregnated with phosphoric acid as disclosed in Knifton U.S. Pat. No. 4,822,921, a hetero polyacid such as 12-tungstophosphoric acid or 12-molybdophosphoric acid supported on titania, etc.

Zeolites, as disclosed in Japanese Patent 0007432, or aluminosilicate zeolites, as disclosed in Chang et al. U.S. Pat. No. 4,058,576, may also be used.

The reaction conditions to be utilized when reacting methanol with tertiary butyl alcohol in the presence of a sulfonic acid resin etherification catalyst include a reaction temperature of about 90° to about 140° C., a pressure of about 30 to about 500 psia and a space velocity of about 0.5 to about 20 volumes of feed per volume of etherification catalyst per hour.

The Finishing Reactor

In accordance with the present invention, isobutylene obtained during the recovery process is brought into contact with a solid resin etherification catalyst in a finishing reactor, in order to convert a significant portion of the isobutylene and methanol to methyl tertiary butyl ether.

Any suitable solid resin etherification catalyst may be used such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Dowex M-31", "Dowex M-32", "Nalcite HCR", "Amberlyst A-15", "Amberlyst A-16". The use of catalyst of this nature is disclosed, for example, in Rao U.S. Pat. No. 4,144,138.

Isobutylene is brought into contact with the solid resin etherification catalyst in the finishing reactor (that can also be considered an isobutylene conversion reactor) under conversion conditions including, for example, a temperature of about 35° to about 130° C., a pressure of about 50 to about 500 psia and a contact time of about 0.5 to about 20 volumes of second distillate fraction per volume of etherification catalyst per hour. As a consequence, an isobutylene conversion product is formed which will normally contain from about 0 to about 10 wt. % of isobutylene, about 75 to about 85 wt. % of methyl tertiary butyl ether and from about 10 to about 15 wt. % of methanol and about 0 to about 2 wt. % of tertiary butyl alcohol.

DESCRIPTION OF THE PREFERRED EMBODIMENT

Figure 1:
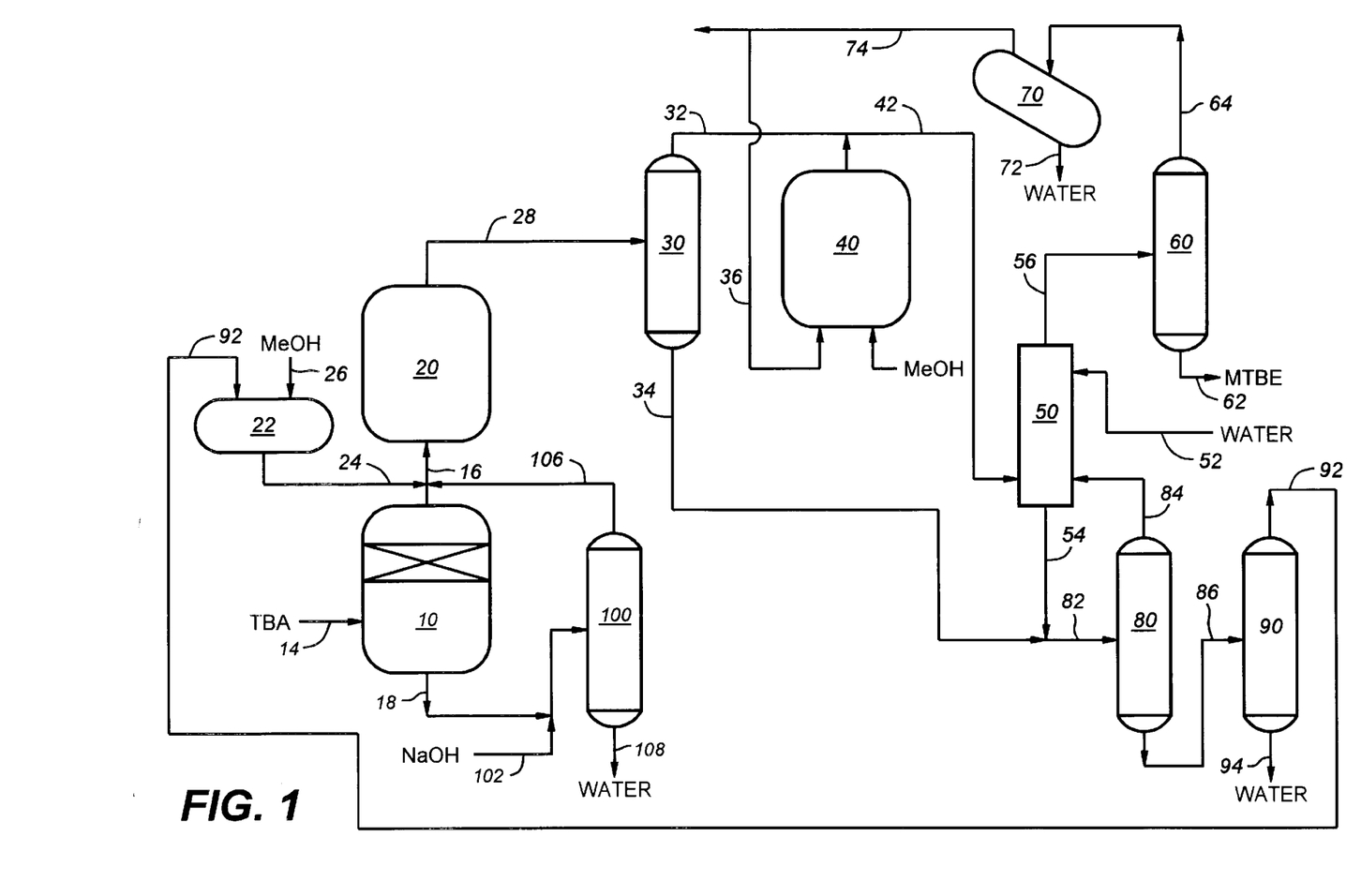
FIG. 1 is a schematic flow sheet with conventional parts omitted showing the general reaction and recovery sequence of the present invention for the manufacture and purification of methyl tertiary butyl ether.

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condensers, reboilers, etc., have been omitted.

In accordance with the present invention, there is provided a reactive distillation column 10 containing a bed of a tertiary butyl alcohol dehydration catalyst. Any suitable tertiary butyl alcohol dehydration catalyst may be used such as a HF treated zeolite catalyst or an HF treated Clay, preferably a HF treated zeolite catalyst.

The contaminated tertiary butyl alcohol feedstock is initially charged by way of a tertiary butyl alcohol feed line 14 to a reactive distillation column 10 operated at a reaction temperature of about 100° to about 180° C., a pressure of about 0 to about 500 psia, a distillation top temperature of about 25° to 60° C. and a distillation bottom temperature of about 70° to about 205° C.

The peroxide contaminants will be decomposed to form acetone, methanol and tertiary butyl alcohol. The formates will be decomposed to form decomposition products such as tertiary butyl alcohol, formic acid, etc.

The tertiary butyl alcohol will be partially dehydrated to form isobutylene and water. Also, the conversion products will be fractionated in the reactive distillation column 10 to provide a lower boiling isobutylene fraction 16 and a higher boiling aqueous TBA fraction 18.

The higher boiling aqueous TBA fraction is discharged from the reactive distillation column 10 by a line 18 leading to a first distillation column 100. The higher boiling aqueous TBA fraction 18 will normally contain minor amounts of acidic by-products formed in the reactive distillation column 10 and in order to prevent and/or inhibit corrosion in the first distillation column 100, a neutralizing agent such as sodium hydroxide, potassium hydroxide, etc., is added to the line 18 by a line 102 in an amount sufficient to neutralize the acidic by-products.

The higher boiling aqueous TBA fraction 18 is separated in the first distillation column 100 into a first lower boiling TBA fraction 106 and a first higher boiling water fraction 108.

The lower boiling isobutylene fraction 16 and the first lower boiling TBA fraction 106 are charged to an etherification reactor 20 together with methanol which is charged by a line 24. The flow of methanol through the line 24 is regulated so that a molar excess of methanol is present in the line 16 leading to the etherification reactor 20, such as, for example, a molar ratio of about 1.1 to about 3 moles of methanol per mol of tertiary butyl alcohol charged by line 106 and isobutylene charged by line 16.

Within the etherification reactor 20, the etherification feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 70° to about 140° C., and still more preferably from about 80° to about 120° C. When the catalyst is a supported phosphorus acid-type catalyst, clay, modified clay, etc. the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 20 and, more preferably from about 1 to about 4 volumes of feed mixture per volume of etherification catalyst per hour.

Within the etherification reaction zone 20, methanol will exothermically react with the tertiary butyl alcohol and isobutylene to form methyl tertiary butyl ether which will be contained in a reaction product discharged from the etherification reactor 20 by way of a line 28 leading to a second methyl tertiary butyl ether (MTBE) distillation column 30.

As a specific example, when the solid etherification catalyst is a sulfonic acid resin such as Amberlyst 15 and when the molar ratio of methanol to tertiary butyl alcohol in the feed mixture charged to the etherification reactor 20 by the line 16 is within the ratio of about 2.0 moles of methanol per mole of isobutylene and tertiary butyl alcohol, and the reaction is conducted at a temperature of about 100° C. at a feed rate of about 2.0 volumes of feed mixture per volume of catalyst per hour, the etherification reaction product may have the composition in part shown by the following table:

| ETHERIFICATION REACTION PRODUCT | |
| --- | --- |
| Component | % |
| Water | 13.7 |
| Methanol | 27.6 |
| Isobutylene | 3.5 |
| TBA[1] | 14.1 |
| MTBE[2] | 34.5 |
| Other[3] | 6.6 |

[1]Tertiary butyl alcohol
[2]Methyl tertiary butyl ether
[3]May include acetone, propanol, ditertiary butyl peroxide, tertiary butyl formate, etc.

The etherification reaction product charged to the second MTBE distillation zone 30 by way of the charge line 28 is fractionated therein under distillation conditions including a liquid reflux temperature of about 40° to about 80° C., a reflux ratio of about 1.0 to about 1.5, a reboiler temperature of about 95° to about 105° C., and a pressure of about 15 to about 60 psia, the distillation condition being selected such that substantially all of the MTBE in the etherification reaction product 20 is taken overhead from the first distillation zone 30 by a line 32 and such that substantially all of the water exits the distillation zone by the line 34. As a consequence, the second lower boiling distillation fraction 32 taken overhead from the distillation zone 30 will be substantially anhydrous and will comprise substantially all of the isobutylene and substantially all of the methyl tertiary butyl ether and some of the methanol charged to the first distillation zone 30. The second higher boiling impure methanol distillation fraction 34 discharged from the second MTBE distillation zone 30 will comprise methanol, tertiary butyl alcohol and water.

In accordance with the present invention, the first distillation fraction 32 is charged to a methanol solvent extraction tower 50 at a point adjacent the bottom thereof together with an isobutylene conversion product 42, to be described hereafter, for countercurrent contact with water introduced into the solvent extraction tower 50 by a charge line 52.

Within the methanol solvent extraction tower 50, solvent extraction conditions are established for countercurrent solvent extraction including a ratio of isobutylene to water within the range of about 0.8 to about 1.8 volumes of isobutylene per volume of water per hour, and more preferably a ratio of about 1.0 to about 1.5 volumes of isobutylene per volume of water. Extractive conditions to be established may suitably include a temperature of about 20° to about 60° C., and more preferably from about 30° to about 40° C., and a pressure of about 50 to about 500 psia, and more preferably from about 50 to about 150 psia.

As a consequence, a supernatant raffinate will be formed which is withdrawn from the methanol solvent extraction tower 50 by line 56 leading to a third distillation zone comprising, for example, distillation column 60 and decanter 70. The extract is discharged from the solvent extraction tower 50 by way of a bottoms charge line 54 leading to a fourth methyl tertiary butyl ether distillation column 80.

Within the third methyl tertiary butyl ether purification distillation column 60, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a third lower boiling aqueous isobutylene distillation fraction 64 discharged from the third distillation column 60 and a third higher boiling methyl tertiary butyl ether product distillation fraction 62 consisting essentially of product, namely methyl tertiary butyl ether.

The third aqueous isobutylene distillation fraction 64 will comprise a mixture of isobutylene and water and is suitably charged to a decantation zone 70 where it can settle to form a supernatant isobutylene phase withdrawn from the decantation zone 70 by way of a line 74. Water is discharged in the decantation zone 70 by way of a water discharge line 72 and is suitably purged from the system.

All or a part of the isobutylene in the line 74 is charged to an isobutylene conversion reactor 40 (i.e., a finishing reactor) by a line 36. Methanol is charged by a line 37 in an amount such that a molar excess of methanol is present in the isobutylene conversion reactor 40 such as, for example, a molar ratio of about 1.1 to about 3 moles of methanol per mol of isobutylene.

Etherification reaction conditions are established in the isobutylene finishing reactor 40 including, for example, a temperature of about 35° to about 130° C., and more preferably from about 40° to about 90° C., a pressure of about 50 to about 500 psia, and more preferably from about 150 to about 250 psia, and a contact time of about 0.5 to about 4 volumes of isobutylene per volume of solid resin etherification catalyst per hour. As a consequence, a portion of the methanol and isobutylene contained in the first distillation fraction 32 will be converted to methyl tertiary butyl ether. Typically, the conversion will amount to about 20 to about 85 wt. %, based on the isobutylene.

Thus, an isobutylene conversion product is formed, which is discharged in the isobutylene conversion reactor 40 by a line 42 leading to a methanol solvent extraction tower 50.

The composition of a representative feedstock and a representative isobutylene conversion product may be characterized as follows:

| ISOBUTYLENE FEEDSTOCK AND CONVERSION PRODUCT | | |
|---|---|---|
| Component | Feed, wt. % | Product, wt. % |
| Water | 0.5 wt. % | 0.4 wt. % |
| Methanol | 13.5 wt. % | 8.0 wt. % |
| Isobutylene | 12.0 wt. % | 2.5 wt. % |
| TBA | 0.9 wt. % | 1.0 wt. % |
| MTBE | 70.4 wt. % | 85.5 wt. % |
| Other | 2.7 wt. % | 2.6 wt. % |

The extract 54 charged to the fourth distillation column 80 will comprise methyl tertiary butyl ether, methanol and water, and is suitably fractionated therein under distillation conditions including a liquid reflux temperature of about 30° to about 90° C., and more preferably from about 50° to about 75° C., and a reboiler temperature of about 80° to about 120° C., and more preferably from about 105° to about 115° C., and a pressure of about 15 to about 60 psia, and more preferably from about 40 to about 50 psia, to form a lower boiling methyl tertiary butyl ether recycle distillation fraction 84 comprising methyl tertiary butyl ether which may suitably be charged to the methanol solvent extraction tower 50. A higher boiling aqueous methanol distillation fraction comprising water and methanol is discharged from the fourth distillation column 80 by a line 86 leading to a fifth distillation column 90. The distillation fraction 86 charged to the fifth methanol distillation column 90 is fractionated therein under distillation conditions which may suitably include a liquid reflux temperature of about 30° to about 80° C., and more preferably from about 60° to about 75° C., a reboiler temperature of about 100° to about 140° C., and more preferably from about 110° to about 120° C., and a pressure of about 15 to about 60 psia, and more preferably from about 20 to about 30 psia, into a fifth lower boiling methanol distillation fraction 92 which may be suitably charged to a charge drum 22 together with fresh methanol charged by a line 26. A fifth higher boiling aqueous distillation fraction consisting essentially of water is discharged from the fifth methanol distillation column 90 by way of a line 94 and may be discharged from the system.

The second higher boiling impure methanol distillation fraction 34 discharged from the second MTBE distillation tower 30 will comprise methanol, tertiary butyl alcohol and water and is charged to the fourth methanol distillation column 80 where it is fractionated in the manner described above.

EXAMPLES

The invention will be further illustrated by the following specific examples, which are given by way of illustration and not as limitations on the scope of the invention. Where parts are mentioned, they are parts by weight.

The experiments described herein were conducted in a pilot unit reactive distillation column comprising a reactive distillation column containing a bed of an isobutylene dehydration catalyst, an upper distillation section containing a distillation packing (e.g., Goodloe packing) and a lower distillation section, also containing distillation packing.

The lower boiling distillation isobutylene reaction product components were flowed upwardly through the upper distillation section to a reflux splitter and then to a reflux condenser where the lower boiling distillation isobutylene reaction product was cooled.

The higher boiling aqueous distillation reaction product flowed downwardly through the lower distillation section to a reboiler where it was heated by an electrical heater. A portion of the higher boiling aqueous distillation reaction product was withdrawn and the remainder of the higher boiling aqueous distillation reaction product was returned to the reactive distillation column by a reboiler return line.

The attached Examples 1–3 illustrate t-butanol dehydration to isobutylene in the reactive distillation unit where, in the presence of zeolite beta, under moderate pressures (0–20 psi) and temperatures (<130° C.), quantitative t-butanol conversion levels were achieved with simultaneous separation of the isobutylene and water fractions as overhead and bottoms products in good selectivities (see Tables 1, 2, and 3). Crude (95%) t-butanol was used as a feedstock, and contained measurable quantities of water, methanol (MeOH), isobutylene ($C_4H_8$), acetone ($AC_2O$), methyl t-butyl ether(MTBE) and methyl ethyl ketone (MEK).

In Example 4, a similar t-butanol dehydration to isobutylene is illustrated using an HF-treated montmorillonite clay catalyst.

In Example 5, t-butanol dehydration is effected using a HF-treated beta zeolite catalyst, again with simultaneous separation of the isobutylene and water coproducts.

In Examples 6–31, t-butanol dehydration is effected with two beta zeolite catalysts over a range of mild operating conditions.

Examples 1–3 (7393-6 and -8)

These examples illustrate the dehydration of tertiary-butanol using reactive distillation equipment and zeolite catalysts.

To the reactive distillation column was charged 350 cc of zeolite beta having a silica-to-alumina mole ratio of 24 and a surface area of 630–650 $m_2/g$ (80% beta, 20% alumina binder) as 1/16" diameter extrudates. The reboiler was filled with aqueous t-butanol, then crude t-butanol (ca. 95%) was continuously charged to the middle of the column, at a rate of ca. 100 cc/hr. The liquid in the reboiler was slowly brought to reflux under 10 psi pressure and product taken off both as overhead lights (T) and as a bottoms fraction (B).

Under steady state conditions, samples of both the overhead and bottoms were collected and analyzed by GLC with a reboiler temperature of 110° C. and a column temperature range of 64°–99° C., a sample (362 g) of overhead product was found to comprise ca. 94% isobutylene. A full analysis may be found in Table 1. The corresponding bottoms product fraction (142 g) was found to be 97% water, containing only 0.2% unreacted t-butanol. Again, analytical details may be found in Table 1.

A second experimental run where the reactive distillation unit was operated under 20 psi pressure and the column and reboiler temperatures were 50°–105° C. and 127° C., respectively, gave very similar results—see Table 2. Here again, the light product fraction comprised ca. 81% isobutylene, while the bottoms liquid was ca. 97% water. t-Butanol conversion was once more close to quantitative.

TABLE 1 t-Butanol Dehydration - Beta Zeolite Catalyst

| | Percentage (%)[a] | | | | | | |
|---|---|---|---|---|---|---|---|
| | $H_2O$ | MeOH | $C_4H_8$ | $AC_2O$ | TBA | MTBE | $C_6H_{16}$ |
| Feed composition | 1.3 | 0.5 | 0.1 | 1.6 | 94.7 | 0.4 | |
| Product-Lights fraction | 0.1 | | 94.4 | 1.6 | | 2.2 | 0.2 |
| Product-Bottoms fraction | 97.2 | | | | 0.2 | 1.4 | 0.6 |

[a]Abbreviations: Methanol (MeOH), Isobutylene ($C_4H_8$), Acetone ($AC_2O$), t-butanol (TBA), methyl t-butyl ether (MTBE), diisobutylene ($C_8H_{16}$).

TABLE 2 t-Butanol Dehydration - Beta Zeolite Catalyst

| | Percentage (%) | | | | | | |
|---|---|---|---|---|---|---|---|
| | $H_2O$ | MeOH | $C_4H_8$ | $AC_2O$ | TBA | MTBE | $C_8H_{16}$ |
| Feed composition | 1.3 | 0.5 | 0.1 | 1.6 | 94.7 | 0.4 | |
| Product-Lights fraction | 0.2 | 0.1 | 80.7 | 0.9 | | 5.1 | 12.4 |
| Product-Bottoms fraction | 96.5 | | | | 0.3 | 1.9 | 0.7 |

A third experimental run, where the reactive distillation unit was operated with zeolite beta catalyst at atmospheric pressure again provided both overhead and bottoms product. With the column and reboiler temperatures set at 70°–80° C. and 78° C., respectively, typical results are summarized in Table 3.

TABLE 3 t-Butanol Dehydration - Beta Zeolite Catalyst

| | Percentage (%) | | | | | | |
|---|---|---|---|---|---|---|---|
| | $H_2O$ | MeOH | $C_4H_8$ | $AC_2O$ | TBA | MTBE | $C_8H_{16}$ |
| Feed composition | 1.3 | 0.5 | 0.1 | 1.6 | 94.7 | 0.4 | |
| Product-Lights fraction | 5.6 | 0.4 | 55.9 | 1.2 | 34.1 | 0.8 | 0.6 |
| Product-Bottoms fraction | 19.0 | | | | 76.1 | 0.1 | 0.7 |

Example 4 (7394-5)

This example illustrates the dehydration of tertiary-butanol using reactive distillation equipment and an HF-treated clay catalyst.

The reactive distillation column was charged with 300 cc of 0.6% HF-treated montmorillonite clay granules (20/60 mesh). The reboiler was filled with aqueous t-butanol and the crude t-butanol feed of Example 1 was continuously charged to the middle of the column at a rate of ca. 100 cc/hr.

Under steady state conditions, with a reboiler temperature of 78° C. and a column temperature range of 37°–83° C., a sample of overhead product showed the presence of significant quantities of isobutylene.

Example 5 (7393-14)

This example illustrates the dehydration of tertiary butanol using reactive distillation equipment and an HF-treated beta zeolite catalyst.

t-Butanol dehydration was conducted using the equipment and procedures of Example 1. The reactive distillation column was charged with 350 cc of 0.9% HF-treated beta zeolites, as 1/16" extrudates. The reboiler was filled with aqueous t-butanol and the crude t-butanol of Example 1 was continuously charged to the middle of the column at the rate of ca. 100 cc/hr.

Under steady state conditions, with a reboiler temperature of 112° C. and a column temperature range of 87°–96° C., typical results are summarized in Table 4.

TABLE 4 t-Butanol Dehydration - HF/Beta Zeolite

Percentage (%)

| | $H_2O$ | MeOH | $C_4H_8$ | $AC_2O$ | TBA | MTBE | $C_8H_{16}$ |
|---|---|---|---|---|---|---|---|
| Feed composition | 1.3 | 0.5 | 0.1 | 1.6 | 94.7 | 0.4 | |
| Product-Lights fraction | 1.3 | 0.5 | 59.9 | 10.7 | 12.7 | 10.3 | 1.2 |
| Product-Bottoms fraction | 95.3 | | | | 0.7 | 1.8 | 1.2 |

Examples 6–15

These examples illustrate the use of a beta zeolite catalyst having a silica-to-alumina mole ratio of 24, in 1/16" diameter extruded form, where t-butanol conversion per pass was up to 96% (Example 7) under mild column temperatures of less than 100° C. Again, the isobutylene was taken off as an overhead fraction in up to 94% purity, while water plus unreacted TBA comprise the principal components of the bottoms take-off liquid.

Data are summarized in Tables 5-1 through 5-5.

TABLE 5-1 tert-Butyl Alcohol Dehydration by Catalytic Distillation

| | 7456-7 | | | 7456-8 | | |
|---|---|---|---|---|---|---|
| | Feed | Bottoms | Traps | Feed | Bottoms | Traps |
| Water | 1.345 | 66.746 | 0.320 | 1.345 | 62.245 | 0.275 |
| Methanol | 0.366 | 0.039 | 0.133 | 0.366 | 0.000 | 0.065 |
| Isobutylene | 0.000 | 0.000 | 93.694 | 0.000 | 0.000 | 93.160 |
| Acetone | 1.364 | 0.850 | 1.595 | 1.364 | 0.046 | 2.294 |
| Isopropanol | 0.324 | 0.387 | 0.044 | 0.324 | 0.567 | 0.026 |
| t-Butyl Alcohol | 94.918 | 30.032 | 2.829 | 94.918 | 34.595 | 2.443 |
| Me-t-Butyl Ether | 0.050 | 0.558 | 1.150 | 0.050 | 0.195 | 1.607 |
| Me Et. Ketone | 0.169 | 0.941 | 0.087 | 0.169 | 1.312 | 0.000 |
| Diisobutylene | 0.061 | 0.000 | 0.000 | 0.061 | 0.451 | 0.000 |
| Unknowns | 1.403 | 0.447 | 0.148 | 1.403 | 0.589 | 0.130 |
| Weight (g) | 329.0 | 141.0 | 269.0 | 616.0 | 33.0 | 513.0 |
| Reactor Conditions: | | | | | | |
| Reboiler Temp., (°C.) | | 99 | | | 99 | |
| Column Bottom, Temp., (°C.) | | 98 | | | 98 | |
| Column Top, Temp., (°C.) | | 50 | | | 67 | |
| Reflux Temp., (°C.) | | 34 | | | 46 | |
| Differential Press. (In.) | | 0 | | | 0 | |
| Reactor Press., (psig) | | 10.7 | | | 9.6 | |
| Feed Rate, (g/hr) | | 103 | | | 108 | |
| Time on Stream (Hr) | | 4.2 | | | 6.0 | |
| Catalyst | | B-Zeolite | | | B-Zeolite | |
| Material Balance, % | | 124.62 | | | 88.64 | |
| t-Butyl Alcohol Conversion, % | | 84.00 | | | 95.90 | |
| Isobutylene Selectivity, % | | 126.94 | | | 112.60 | |
| Water Selectivity, % | | 142.01 | | | 10.03 | |
| Diisobutylene Selectivity, % | | −0.05 | | | −0.03 | |

TABLE 5-2 tert-Butyl Alcohol Dehydration by Catalytic Distillation

|  | 7456-9 | | | 7456-10 | | |
| --- | --- | --- | --- | --- | --- | --- |
|  | Feed | Bottoms | Traps | Feed | Bottoms | Traps |
| Water | 1.345 | 77.825 | 0.000 | 1.890 | 59.870 | 0.210 |
| Methanol | 0.366 | 0.000 | 0.043 | 0.355 | 0.061 | 0.061 |
| Isobutylene | 0.000 | 0.000 | 93.340 | 0.000 | 0.000 | 90.416 |
| Acetone | 1.364 | 0.018 | 1.746 | 1.249 | 0.097 | 2.778 |
| Isopropanol | 0.324 | 0.508 | 0.038 | 0.323 | 0.657 | 0.079 |
| t-Butyl Alcohol | 94.918 | 18.746 | 3.170 | 94.540 | 37.756 | 3.709 |
| Me-t-Butyl Ether | 0.050 | 0.216 | 1.312 | 0.056 | 0.214 | 2.310 |
| Me Et. Ketone | 0.169 | 1.061 | 0.000 | 0.157 | 1.131 | 0.000 |
| Diisobutylene | 0.061 | 0.899 | 0.080 | 0.000 | 0.000 | 0.162 |
| Unknowns | 1.403 | 0.727 | 0.271 | 1.430 | 0.214 | 0.275 |
| Weight (g) | 843.0 | 95.0 | 549.0 | 1118.0 | 533.0 | 481.0 |
| Reactor Conditions: | | | | | | |
| Reboiler Temp., (°C.) | 99 | | | 96 | | |
| Column Bottom, Temp., (°C.) | 97 | | | 95 | | |
| Column Top, Temp., (°C.) | 72 | | | 53 | | |
| Reflux Temp., (°C.) | 51 | | | 43 | | |
| Differential Press. (In.) | 0 | | | 0 | | |
| Reactor Press., (psig) | 8.3 | | | 7.8 | | |
| Feed Rate, (g/hr) | 146 | | | 195 | | |
| Time on Stream (Hr) | 6.0 | | | 5.0 | | |
| Catalyst | B-Zeolite | | | B-Zeolite | | |
| Material Balance, % | 76.39 | | | 90.70 | | |
| t-Butyl Alcohol Conversion, % | 95.60 | | | 79.27 | | |
| Isobutylene Selectivity, % | 88.51 | | | 68.58 | | |
| Water Selectivity, % | 33.67 | | | 146.81 | | |
| Diisobutylene Selectivity, % | 0.07 | | | 0.06 | | |

TABLE 5-3 tert-Butyl Alcohol Dehydration by Catalytic Distillation

|  | 7456-11 | | | 7456-14 | | |
| --- | --- | --- | --- | --- | --- | --- |
|  | Feed | Bottoms | Traps | Feed | Bottoms | Traps |
| Water | 1.437 | 35.397 | 0.859 | 1.562 | 38.555 | 1.643 |
| Methanol | 0.367 | 0.000 | 0.000 | 0.325 | 0.099 | 0.107 |
| Isobutylene | 0.000 | 0.069 | 92.193 | 0.000 | 0.000 | 92.495 |
| Acetone | 1.255 | 0.065 | 2.410 | 1.167 | 0.144 | 2.465 |
| Isopropanol | 0.320 | 0.661 | 0.046 | 0.306 | 0.688 | 0.036 |
| t-Butyl Alcohol | 94.934 | 61.644 | 1.868 | 95.332 | 59.034 | 1.573 |
| Me-t-Butyl Ether | 0.042 | 0.061 | 2.311 | 0.052 | 0.110 | 1.517 |
| Me Et. Ketone | 0.164 | 1.467 | 0.000 | 0.150 | 0.074 | 0.000 |
| Diisobutylene | 0.039 | 0.000 | 0.000 | 0.000 | 0.000 | 0.000 |
| Unknowns | 1.442 | 0.636 | 0.313 | 1.106 | 1.296 | 0.164 |
| Weight (g) | 1158.0 | 581.0 | 636.0 | 1179.0 | 553.0 | 510.0 |
| Reactor Conditions: | | | | | | |
| Reboiler Temp., (°C.) | 96 | | | 95 | | |
| Column Bottom, Temp., (°C.) | 97 | | | 95 | | |
| Column Top, Temp., (°C.) | 75 | | | 78 | | |
| Reflux Temp., (°C.) | 55 | | | 57 | | |
| Differential Press. (In.) | 0 | | | | | |
| Reactor Press., (psig) | 9.6 | | | 8.2 | | |
| Feed Rate, (g/hr) | 202 | | | 192 | | |
| Time on Stream (Hr) | 6.0 | | | 6.2 | | |
| Catalyst | B-Zeolite | | | B-Zeolite | | |
| Material Balance, % | 105.09 | | | 90.16 | | |
| t-Butyl Alcohol Conversion, % | 66.34 | | | 70.24 | | |
| Isobutylene Selectivity, % | 106.30 | | | 78.94 | | |
| Water Selectivity, % | 109.71 | | | 105.88 | | |
| Diisobutylene Selectivity, % | −0.04 | | | 0.00 | | |

TABLE 5-4 tert-Butyl Alcohol Dehydration by Catalytic Distillation

|  | 7456-15 | | | 7456-17 | | |
|---|---|---|---|---|---|---|
|  | Feed | Bottoms | Traps | Feed | Bottoms | Traps |
| Water | 1.355 | 36.090 | 1.388 | 1.223 | 42.905 | 0.259 |
| Methanol | 0.352 | 0.010 | 0.110 | 0.390 | 0.080 | 0.087 |
| Isobutylene | 0.000 | 0.000 | 93.263 | 0.000 | 0.000 | 89.714 |
| Acetone | 1.280 | 0.807 | 2.299 | 1.518 | 0.029 | 3.483 |
| Isopropanol | 0.328 | 0.000 | 0.031 | 0.370 | 0.531 | 0.067 |
| t-Butyl Alcohol | 94.894 | 61.403 | 1.265 | 94.957 | 55.303 | 3.654 |
| Me-t-Butyl Ether | 0.000 | 0.068 | 1.559 | 0.000 | 0.057 | 2.260 |
| Me Et. Ketone | 0.345 | 0.050 | 0.000 | 0.000 | 0.036 | 0.000 |
| Diisobutylene | 0.000 | 0.051 | 0.000 | 0.000 | 0.000 | 0.065 |
| Unknowns | 1.446 | 1.521 | 0.085 | 1.542 | 1.059 | 0.411 |
| Weight (g) | 1174.0 | 561.0 | 625.0 | 519.0 | 290.0 | 183.0 |
| Reactor Conditions: | | | | | | |
| Reboiler Temp., (°C.) | | 96 | | | 81 | |
| Column Bottom, Temp., (°C.) | | 95 | | | 83 | |
| Column Top, Temp., (°C.) | | 78 | | | 76 | |
| Reflux Temp., (°C.) | | 71 | | | 75 | |
| Differential Press. (In.) | | 0 | | | 7 | |
| Reactor Press., (psig) | | 8.1 | | | 0 | |
| Feed Rate, (g/hr) | | 199 | | | 187 | |
| Time on Stream (Hr) | | 6.2 | | | 4.2 | |
| Catalyst | | B-Zeolite | | | B-Zeolite | |
| Material Balance, % | | 101.02 | | | 91.14 | |
| t-Butyl Alcohol Conversion, % | | 68.37 | | | 66.10 | |
| Isobutylene Selectivity, % | | 101.11 | | | 66.59 | |
| Water Selectivity, % | | 105.45 | | | 149.72 | |
| Diisobutylene Selectivity, % | | 0.02 | | | 0.02 | |

TABLE 5-5 tert-Butyl Alcohol Dehydration by Catalytic Distillation

|  | 7456-18 | | | 7456-19 | | |
|---|---|---|---|---|---|---|
|  | Feed | Bottoms | Traps | Feed | Bottoms | Traps |
| Water | 1.511 | 23.186 | 0.000 | 1.133 | 19.147 | 0.000 |
| Methanol | 0.402 | 0.080 | 0.000 | 0.384 | 0.065 | 0.059 |
| Isobutylene | 0.004 | 0.000 | 85.145 | 0.004 | 0.000 | 89.598 |
| Acetone | 1.550 | 0.153 | 4.499 | 1.524 | 0.052 | 3.380 |
| Isopropanol | 0.367 | 0.529 | 0.068 | 0.365 | 0.481 | 0.070 |
| t-Butyl Alcohol | 94.482 | 74.934 | 3.455 | 95.001 | 79.259 | 4.313 |
| Me-t-Butyl Ether | 0.023 | 0.021 | 5.204 | 0.000 | 0.019 | 1.981 |
| Me Et. Ketone | 0.000 | 0.021 | 0.000 | 0.000 | 0.038 | 0.000 |
| Diisobutylene | 0.066 | 0.107 | 0.122 | 0.048 | 0.000 | 0.000 |
| Unknowns | 1.595 | 0.969 | 1.507 | 1.541 | 0.939 | 0.599 |
| Weight (g) | 728.0 | 379.0 | 200.0 | 712.0 | 491.0 | 174.0 |
| Reactor Conditions: | | | | | | |
| Reboiler Temp., (°C.) | | 81 | | | 80 | |
| Column Bottom, Temp., (°C.) | | 83 | | | 80 | |
| Column Top, Temp., (°C.) | | 76 | | | 31 | |
| Reflux Temp., (°C.) | | 74 | | | 30 | |
| Differential Press. (In.) | | 4.5 | | | 0 | |
| Reactor Press., (psig) | | 0 | | | 0 | |
| Feed Rate, (g/hr) | | 100 | | | 198 | |
| Time on Stream (Hr) | | 5.5 | | | 6.0 | |
| Catalyst | | B-Zeolite | | | B-Zeolite | |
| Material Balance, % | | 79.53 | | | 93.40 | |
| t-Butyl Alcohol Conversion, % | | 57.71 | | | 41.36 | |
| Isobutylene Selectivity, % | | 56.67 | | | 73.62 | |
| Water Selectivity, % | | 79.68 | | | 126.40 | |
| Diisobutylene Selectivity, % | | 0.03 | | | −0.08 | |

Examples 16–31

These examples illustrate the use of an alternative beta zeolite catalyst in 1/16" diameter extruded form where t-butanol conversion levels to 89% (Example 16) are achieved over a range of mild operating conditions.

Data are summarized in Tables 6-1 through 6-8.

TABLE 6-1 tert-Butyl Alcohol Dehydration by Catalytic Distillation

| | 7456-28 | | | 7456-29 | | |
|---|---|---|---|---|---|---|
| | Feed | Bottoms | Traps | Feed | Bottoms | Traps |
| Water | 1.196 | 56.776 | 0.000 | 1.342 | 40.659 | 1.878 |
| Methanol | 0.393 | 0.000 | 0.000 | 0.391 | 0.000 | 0.000 |
| Isobutylene | 0.000 | 0.152 | 76.905 | 0.000 | 0.061 | 79.611 |
| Acetone | 0.187 | 0.000 | 0.000 | 0.190 | 0.000 | 0.099 |
| Isopropanol | 1.546 | 0.932 | 8.442 | 1.540 | 0.130 | 6.031 |
| t-Butyl Alcohol | 94.858 | 40.046 | 6.137 | 94.129 | 57.355 | 5.933 |
| Me-t-Butyl Ether | 0.019 | 0.171 | 6.250 | 0.016 | 0.068 | 4.536 |
| Me Et. Ketone | 0.153 | 0.171 | 0.000 | 0.163 | 1.059 | 0.427 |
| Diisobutylene | 0.054 | 0.532 | 0.345 | 0.028 | 0.000 | 0.000 |
| Unknowns | 1.594 | 1.220 | 1.921 | 2.201 | 0.668 | 1.485 |
| Weight (g) | 648.0 | 112.0 | 362.0 | 464.0 | 243.0 | 131.0 |
| Reactor Conditions: | | | | | | |
| Reboiler Temp., (°C.) | 82 | | | 82 | | |
| Column Bottom, Temp., (°C.) | 83 | | | 83 | | |
| Column Top, Temp., (°C.) | 67 | | | 76 | | |
| Reflux Temp., (°C.) | 46 | | | 74 | | |
| Differential Press. (In.) | 9.3 | | | 8.6 | | |
| Reactor Press., (psig) | 0 | | | 0 | | |
| Feed Rate, (g/hr) | 103 | | | 102 | | |
| Time on Stream (Hr) | 6.0 | | | 5.0 | | |
| Catalyst | Beta Zeolite 1/16" | | | Beta Zeolite 1/16" | | |
| Material Balance, % | 73.15 | | | 80.60 | | |
| t-Butyl Alcohol Conversion, % | 89.09 | | | 66.31 | | |
| Isobutylene Selectivity, % | 67.21 | | | 47.64 | | |
| Water Selectivity, % | 41.95 | | | 135.00 | | |
| Diisobutylene Selectivity, % | 0.18 | | | −0.03 | | |

TABLE 6-2 tert-Butyl Alcohol Dehydration by Catalytic Distillation

| | 7456-30 | | | 7456-31 | | |
|---|---|---|---|---|---|---|
| | Feed | Bottoms | Traps | Feed | Bottoms | Traps |
| Water | 1.089 | 34.010 | 0.578 | 1.247 | 53.312 | 0.449 |
| Methanol | 0.390 | 0.000 | 0.000 | 0.397 | 0.000 | 0.000 |
| Isobutylene | 0.000 | 0.028 | 94.022 | 0.000 | 0.000 | 93.245 |
| Acetone | 0.271 | 0.000 | 0.022 | 0.192 | 0.000 | 0.020 |
| Isopropanol | 2.324 | 0.017 | 1.822 | 1.558 | 0.153 | 2.445 |
| t-Butyl Alcohol | 93.282 | 64.180 | 1.816 | 94.811 | 44.397 | 1.903 |
| Me-t-Butyl Ether | 0.016 | 0.067 | 1.477 | 0.021 | 0.071 | 1.323 |
| Me Et. Ketone | 0.221 | 0.962 | 0.000 | 0.161 | 1.100 | 0.000 |
| Diisobutylene | 0.000 | 0.000 | 0.091 | 0.027 | 0.000 | 0.008 |
| Unknowns | 2.407 | 0.736 | 0.172 | 1.586 | 0.967 | 0.607 |
| Weight (g) | 441.0 | 212.0 | 322.0 | 1174.0 | 569.0 | 580.0 |
| Reactor Conditions: | | | | | | |
| Reboiler Temp., (°C.) | 97 | | | 100 | | |
| Column Bottom, Temp., (°C.) | 96 | | | 100 | | |
| Column Top, Temp., (°C.) | 63 | | | 89 | | |
| Reflux Temp., (°C.) | 35 | | | 56 | | |
| Differential Press. (In.) | 0 | | | 2 | | |
| Reactor Press., (psig) | 9.4 | | | 10.5 | | |
| Feed Rate, (g/hr) | 99 | | | 203 | | |
| Time on Stream (Hr) | 5.2 | | | 6.0 | | |
| Catalyst | Beta Zeolite 1/16" | | | Beta Zeolite 1/16" | | |
| Material Balance, % | 121.09 | | | 97.87 | | |
| t-Butyl Alcohol Conversion, % | 65.50 | | | 76.31 | | |
| Isobutylene Selectivity, % | 148.47 | | | 84.12 | | |
| Water Selectivity, % | 105.59 | | | 141.09 | | |
| Diisobutylene Selectivity, % | 0.07 | | | −0.02 | | |

TABLE 6-3 tert-Butyl Alcohol Dehydration by Catalytic Distillation

|  | 7456-32 | | | 7456-33 | | |
| --- | --- | --- | --- | --- | --- | --- |
|  | Feed | Bottoms | Traps | Feed | Bottoms | Traps |
| Water | 1.066 | 34.689 | 0.194 | 1.123 | 28.010 | 0.075 |
| Methanol | 0.409 | 0.000 | 0.000 | 0.425 | 0.000 | 0.067 |
| Isobutylene | 0.000 | 0.047 | 92.533 | 0.000 | 0.041 | 91.169 |
| Acetone | 0.202 | 0.000 | 0.047 | 0.186 | 0.000 | 0.015 |
| Isopropanol | 1.691 | 0.036 | 3.410 | 1.759 | 0.044 | 3.971 |
| t-Butyl Alcohol | 94.753 | 62.488 | 1.384 | 94.690 | 69.719 | 2.232 |
| Me-t-Butyl Ether | 0.000 | 0.062 | 2.252 | 0.019 | 0.062 | 1.947 |
| Me Et. Ketone | 0.173 | 1.331 | 0.000 | 0.162 | 0.899 | 0.012 |
| Diisobutylene | 0.000 | 0.265 | 0.000 | 0.057 | 0.250 | 0.029 |
| Unknowns | 1.706 | 1.082 | 0.180 | 1.579 | 0.975 | 0.483 |
| Weight (g) | 1222.0 | 489.0 | 665.0 | 1192.0 | 686.0 | 493.0 |
| Reactor Conditions: | | | | | | |
| Reboiler Temp., (°C.) | 97 | | | 97 | | |
| Column Bottom, Temp., (°C.) | 98 | | | 98 | | |
| Column Top, Temp., (°C.) | 87 | | | 86 | | |
| Reflux Temp., (°C.) | 78 | | | 79 | | |
| Differential Press. (In.) | 0 | | | 0 | | |
| Reactor Press., (psig) | 9.9 | | | 10.8 | | |
| Feed Rate, (g/hr) | 192 | | | 201 | | |
| Time on Stream (Hr) | 6.5 | | | 6.2 | | |
| Catalyst | Beta Zeolite 1/16" | | | Beta Zeolite 1/16" | | |
| Material Balance, % | 94.44 | | | 98.91 | | |
| t-Butyl Alcohol Conversion, % | 72.82 | | | 56.65 | | |
| Isobutylene Selectivity, % | 96.46 | | | 92.93 | | |
| Water Selectivity, % | 77.05 | | | 115.25 | | |
| Diisobutylene Selectivity, % | 0.10 | | | 0.12 | | |

TABLE 6-4 tert-Butyl Alcohol Dehydration by Catalytic Distillation

|  | 7456-34 | | | 7456-35 | | |
| --- | --- | --- | --- | --- | --- | --- |
|  | Feed | Bottoms | Traps | Feed | Bottoms | Traps |
| Water | 1.117 | 29.145 | 0.127 | 1.182 | 29.422 | 0.114 |
| Methanol | 0.443 | 0.000 | 0.215 | 0.439 | 0.000 | 0.225 |
| Isobutylene | 0.000 | 0.018 | 87.969 | 0.000 | 0.000 | 89.814 |
| Acetone | 0.187 | 0.000 | 0.000 | 0.184 | 0.000 | 0.000 |
| Isopropanol | 1.733 | 0.135 | 3.357 | 1.744 | 0.254 | 0.000 |
| t-Butyl Alcohol | 94.572 | 68.154 | 2.662 | 94.584 | 67.415 | 3.451 |
| Me-t-Butyl Ether | 0.020 | 0.019 | 1.571 | 0.021 | 0.213 | 1.153 |
| Me Et. Ketone | 0.225 | 1.053 | 0.000 | 0.021 | 0.987 | 0.000 |
| Diisobutylene | 0.062 | 0.271 | 3.823 | 0.084 | 0.178 | 1.688 |
| Unknowns | 1.641 | 1.205 | 0.276 | 1.741 | 1.531 | 3.555 |
| Weight (g) | 1076.0 | 682.0 | 408.0 | 1091.0 | 463.0 | 404.0 |
| Reactor Conditions: | | | | | | |
| Reboiler Temp., (°C.) | 115 | | | 115 | | |
| Column Bottom, Temp., (°C.) | 112 | | | 112 | | |
| Column Top, Temp., (°C.) | 101 | | | 99 | | |
| Reflux Temp., (°C.) | 68 | | | 54 | | |
| Differential Press. (In.) | 6.1 | | | 4.9 | | |
| Reactor Press., (psig) | 29.7 | | | 30.2 | | |
| Feed Rate, (g/hr) | 195 | | | 196 | | |
| Time on Stream (Hr) | 5.5 | | | 6.0 | | |
| Catalyst | Beta Zeolite 1/16" | | | Beta Zeolite 1/16" | | |
| Material Balance, % | 101.30 | | | 79.47 | | |
| t-Butyl Alcohol Conversion, % | 53.26 | | | 68.40 | | |
| Isobutylene Selectivity, % | 87.53 | | | 67.92 | | |
| Water Selectivity, % | 142.17 | | | 72.15 | | |
| Diisobutylene Selectivity, % | 2.05 | | | 0.63 | | |

TABLE 6-5 tert-Butyl Alcohol Dehydration by Catalytic Distillation

| | 7456-37 | | | 7456-38 | | |
|---|---|---|---|---|---|---|
| | Feed | Bottoms | Traps | Feed | Bottoms | Traps |
| Water | 1.175 | 59.313 | 0.865 | 1.173 | 45.244 | 0.186 |
| Methanol | 0.419 | 0.000 | 0.139 | 0.429 | 0.000 | 0.000 |
| Isobutylene | 0.000 | 0.088 | 94.240 | 0.000 | 0.085 | 94.862 |
| Acetone | 0.167 | 0.000 | 0.010 | 0.174 | 0.000 | 0.000 |
| Isopropanol | 1.703 | 0.244 | 2.141 | 1.713 | 0.170 | 2.428 |
| t-Butyl Alcohol | 94.699 | 37.750 | 1.308 | 94.640 | 52.470 | 1.521 |
| Me-t-Butyl Ether | 0.020 | 0.082 | 1.208 | 0.020 | 0.044 | 0.771 |
| Me Et. Ketone | 0.162 | 1.150 | 0.000 | 0.165 | 0.994 | 0.004 |
| Diisobutylene | 0.053 | 0.339 | 0.000 | 0.058 | 0.000 | 0.000 |
| Unknowns | 1.602 | 1.034 | 0.089 | 1.628 | 0.993 | 0.228 |
| Weight (g) | 1193.0 | 392.0 | 837.0 | 1096.0 | 430.0 | 467.0 |
| Reactor Conditions: | | | | | | |
| Reboiler Temp., (°C.) | 108 | | | 107 | | |
| Column Bottom, Temp., (°C.) | 107 | | | 105 | | |
| Column Top, Temp., (°C.) | 89 | | | 68 | | |
| Reflux Temp., (°C.) | 75 | | | 46 | | |
| Differential Press. (In.) | 0 | | | 1.3 | | |
| Reactor Press., (psig) | 20.7 | | | 20.4 | | |
| Feed Rate, (g/hr) | 199 | | | 200 | | |
| Time on Stream (Hr) | 6.0 | | | 5.0 | | |
| Catalyst | Beta Zeolite 1/16" | | | Beta Zeolite 1/16" | | |
| Material Balance, % | 103.02 | | | 81.84 | | |
| t-Butyl Alcohol Conversion, % | 85.93 | | | 77.56 | | |
| Isobutylene Selectivity, % | 107.39 | | | 72.81 | | |
| Water Selectivity, % | 95.66 | | | 93.36 | | |
| Diisobutylene Selectivity, % | 0.05 | | | −0.05 | | |

TABLE 6-6 tert-Butyl Alcohol Dehydration by Catalytic Distillation

| | 7456-39 | | | 7456-41 | | |
|---|---|---|---|---|---|---|
| | Feed | Bottoms | Traps | Feed | Bottoms | Traps |
| Water | 1.123 | 39.144 | 0.103 | 1.158 | 66.315 | 0.055 |
| Methanol | 0.427 | 0.000 | 0.000 | 0.432 | 0.000 | 0.000 |
| Isobutylene | 0.000 | 0.038 | 92.814 | 0.000 | 0.023 | 96.217 |
| Acetone | 0.178 | 0.000 | 0.026 | 0.174 | 0.000 | 0.000 |
| Isopropanol | 1.760 | 0.219 | 3.451 | 1.714 | 0.161 | 2.246 |
| t-Butyl Alcohol | 94.723 | 57.285 | 1.808 | 94.662 | 30.448 | 0.542 |
| Me-t-Butyl Ether | 0.018 | 0.111 | 1.418 | 0.020 | 0.102 | 0.700 |
| Me Et. Ketone | 0.159 | 1.399 | 0.008 | 0.162 | 1.125 | 0.000 |
| Diisobutylene | 0.000 | 0.291 | 0.000 | 0.060 | 0.487 | 0.000 |
| Unknowns | 1.612 | 1.513 | 0.372 | 1.618 | 1.339 | 0.240 |
| Weight (g) | 994.0 | 437.0 | 545.0 | 1090.0 | 585.0 | 621.0 |
| Reactor Conditions: | | | | | | |
| Reboiler Temp., (°C.) | 106 | | | 108 | | |
| Column Bottom, Temp., (°C.) | 104 | | | 107 | | |
| Column Top, Temp., (°C.) | 89 | | | 85 | | |
| Reflux Temp., (°C.) | 79 | | | 71 | | |
| Differential Press. (In.) | 3.9 | | | 0 | | |
| Reactor Press., (psig) | 19.8 | | | 21.8 | | |
| Feed Rate, (g/hr) | 202 | | | 197 | | |
| Time on Stream (Hr) | 5.0 | | | 5.5 | | |
| Catalyst | Beta Zeolite 1/16" | | | Beta Zeolite 1/16" | | |
| Material Balance, % | 98.79 | | | 110.64 | | |
| t-Butyl Alcohol Conversion, % | 72.37 | | | 82.41 | | |
| Isobutylene Selectivity, % | 98.12 | | | 92.86 | | |
| Water Selectivity, % | 96.89 | | | 181.76 | | |
| Diisobutylene Selectivity, % | 0.12 | | | 0.17 | | |

TABLE 6-7 tert-Butyl Alcohol Dehydration by Catalytic Distillation

|  | 7456-42 | | | 7456-43 | | |
| --- | --- | --- | --- | --- | --- | --- |
|  | Feed | Bottoms | Traps | Feed | Bottoms | Traps |
| Water | 1.013 | 38.921 | 0.039 | 1.012 | 33.804 | 0.050 |
| Methanol | 0.445 | 0.000 | 0.000 | 0.450 | 0.224 | 0.000 |
| Isobutylene | 0.000 | 0.050 | 96.761 | 0.000 | 0.000 | 96.182 |
| Acetone | 0.181 | 0.000 | 0.000 | 0.169 | 0.000 | 0.000 |
| Isopropanol | 1.722 | 0.176 | 2.009 | 1.708 | 0.493 | 1.852 |
| t-Butyl Alcohol | 94.762 | 58.205 | 0.458 | 94.809 | 62.976 | 1.217 |
| Me-t-Butyl Ether | 0.014 | 0.196 | 0.554 | 0.019 | 0.150 | 0.436 |
| Me Et. Ketone | 0.167 | 1.188 | 0.000 | 0.211 | 1.079 | 0.000 |
| Diisobutylene | 0.057 | 0.000 | 0.000 | 0.000 | 0.000 | 0.000 |
| Unknowns | 1.639 | 1.264 | 0.179 | 1.622 | 1.274 | 0.263 |
| Weight (g) | 1045.0 | 438.0 | 574.0 | 1132.0 | 533.0 | 544.0 |
| Reactor Conditions: | | | | | | |
| Reboiler Temp., (°C.) | 108 | | | 107 | | |
| Column Bottom, Temp., (°C.) | 106 | | | 106 | | |
| Column Top, Temp., (°C.) | 65 | | | 87 | | |
| Reflux Temp., (°C.) | 40 | | | 79 | | |
| Differential Press. (In.) | 0 | | | 5.2 | | |
| Reactor Press., (psig) | 21.6 | | | 20.4 | | |
| Feed Rate, (g/hr) | 196 | | | 193 | | |
| Time on Stream (Hr) | 5.0 | | | 6.0 | | |
| Catalyst | Beta Zeolite 1/16" | | | Beta Zeolite 1/16" | | |
| Material Balance, % | 96.84 | | | 95.14 | | |
| t-Butyl Alcohol Conversion, % | 73.99 | | | 68.11 | | |
| Isobutylene Selectivity, % | 100.19 | | | 94.57 | | |
| Water Selectivity, % | 89.90 | | | 95.12 | | |
| Diisobutylene Selectivity, % | −0.05 | | | 0.00 | | |

TABLE 6-8 tert-Butyl Alcohol Dehydration by Catalytic Distillation

|  | 7456-44 | | | 7456-48 | | |
| --- | --- | --- | --- | --- | --- | --- |
|  | Feed | Bottoms | Traps | Feed | Bottoms | Traps |
| Water | 1.064 | 23.211 | 0.020 | 1.029 | 12.737 | 0.251 |
| Methanol | 0.457 | 0.000 | 0.000 | 0.452 | 0.190 | 0.000 |
| Isobutylene | 0.000 | 0.179 | 94.908 | 0.000 | 4.630 | 94.899 |
| Acetone | 1.549 | 0.000 | 3.353 | 1.792 | 0.986 | 1.782 |
| Isopropanol | 0.384 | 0.661 | 0.000 | 0.340 | 0.295 | 0.096 |
| t-Butyl Alcohol | 95.010 | 74.546 | 0.153 | 94.861 | 80.737 | 2.464 |
| Me-t-Butyl Ether | 0.000 | 0.021 | 1.346 | 0.000 | 0.000 | 0.355 |
| Me Et. Ketone | 0.162 | 0.268 | 0.000 | 0.167 | 0.082 | 0.000 |
| Diisobutylene | 0.000 | 0.000 | 0.000 | 0.000 | 0.000 | 0.000 |
| Unknowns | 1.374 | 1.114 | 0.220 | 1.359 | 0.343 | 0.153 |
| Weight (g) | 1119.0 | 724.0 | 363.0 | 442.0 | 333.0 | 59.0 |
| Reactor Conditions: | | | | | | |
| Reboiler Temp., (°C.) | 107 | | | 96 | | |
| Column Bottom, Temp., (°C.) | 106 | | | 43 | | |
| Column Top, Temp., (°C.) | 70 | | | 27 | | |
| Reflux Temp., (°C.) | 46 | | | 23 | | |
| Differential Press. (In.) | 0 | | | 0 | | |
| Reactor Press., (psig) | 20.7 | | | 10.3 | | |
| Feed Rate, (g/hr) | 195 | | | 104 | | |
| Time on Stream (Hr) | 6.0 | | | 4.5 | | |
| Catalyst | Beta Zeolite 1/16" | | | Alumina Support | | |
| Material Balance, % | 97.14 | | | 88.69 | | |
| t-Butyl Alcohol Conversion, % | 49.18 | | | 35.53 | | |
| Isobutylene Selectivity, % | 87.38 | | | 63.33 | | |
| Water Selectivity, % | 122.91 | | | 104.98 | | |
| Diisobutylene Selectivity, % | 0.00 | | | 0.00 | | |

We claim:

1. A process for the preparation of methyl tertiary butyl ether from methanol and tertiary butyl alcohol contaminated with oxygen-containing impurities which comprise the steps of:

a) charging tertiary butyl alcohol contaminated with oxygen-containing impurities to a reactive distillation column containing a bed of a tertiary butyl alcohol dehydration catalyst to decompose the oxygen-containing contaminants, to dehydrate a portion of the tertiary butyl alcohol to form isobutylene and water, and to separate the dehydration reaction products in the reactive distillation column into a lower boiling isobutylene fraction and a higher boiling aqueous tertiary butyl alcohol fraction;

b) distilling the higher boiling aqueous tertiary butyl alcohol fraction in a first distillation column to form a first lower boiling tertiary butyl alcohol fraction and a first higher boiling water fraction;

c) charging the lower boiling isobutylene fraction, the first lower boiling tertiary butyl alcohol fraction and methanol to an etherification reactor to form an etherification reaction product comprising unreacted methanol, unreacted tertiary butyl alcohol, water, isobutylene and methyl tertiary butyl ether;

d) distilling the etherification reaction product in a second distillation column to provide a second lower boiling isobutylene fraction comprising isobutylene, methanol and methyl tertiary butyl ether and a second higher boiling methanol distillation fraction comprising methanol, tertiary butyl alcohol and water;

e) charging the second lower boiling isobutylene fraction to a methanol solvent extraction tower for countercurrent contact with water to form a raffinate comprising MTBE, isobutylene and water and an extract comprising MTBE, methanol and water;

f) charging the raffinate to a third distillation column and separating it therein into a third higher boiling MTBE product fraction and a third lower boiling aqueous isobutylene fraction;

g) charging the third lower boiling aqueous isobutylene fraction to a decantation zone and separating it therein into an isobutylene chase and water;

h) charging the isobutylene phase and methanol to an isobutylene conversion reactor and reacting the isobutylene with methanol to form an isobutylene conversion product comprising methyl tertiary butyl ether, unreacted methanol, unreacted isobutylene and tertiary butyl alcohol; and i) recovering MTBE from the etherification reaction product and the isobutylene conversion product.

2. A method as in claim 1 which comprises the additional steps of:

i) charging the second higher boiling methanol distillation fraction from the second distillation column and the extract from the methanol solvent extraction tower to a fourth distillation column and separating them therein into a fourth lower boiling MTBE fraction and a fourth higher boiling aqueous methanol fraction;

j) recycling the fourth lower boiling MTBE fraction to the methanol solvent extraction tower; and k) separating methanol from the water in the fourth higher boiling aqueous methanol fraction and recycling the separated methanol to the etherification reactor.

3. A process for the preparation of methyl tertiary butyl ether from methanol and tertiary butyl alcohol contaminated with oxygen-containing impurities which comprise the steps of:

a) charging tertiary butyl alcohol contaminated with oxygen-containing impurities to a reactive distillation column containing a bed of a tertiary butyl alcohol dehydration catalyst to decompose the oxygen-containing contaminants, to dehydrate a portion of the tertiary butyl alcohol to form isobutylene and water, and to separate the dehydration reaction products in the reactive distillation column into a lower boiling isobutylene fraction and a higher boiling aqueous tertiary butyl alcohol fraction;

b) distilling the higher boiling aqueous tertiary butyl alcohol fraction in a first distillation column to form a first lower boiling tertiary butyl alcohol fraction and a first higher boiling water fraction;

c) charging the lower boiling isobutylene fraction from the reactive distillation column, the first lower boiling tertiary butyl alcohol fraction and methanol to an etherification reactor and reacting them therein to form an etherification reaction product comprising unreacted methanol, unreacted tertiary butyl alcohol, water, isobutylene and methyl tertiary butyl ether;

d) distilling the etherification reaction product in a second distillation column to provide a second lower boiling isobutylene fraction comprising isobutylene, methanol and methyl tertiary butyl ether and a second higher boiling methanol distillation fraction comprising methanol, tertiary butyl alcohol and water;

e) charging the second lower boiling isobutylene fraction and an isobutylene conversion product to a methanol solvent extraction tower for countercurrent contact with water to form a raffinate comprising MTBE, isobutylene and water and an extract comprising MTBE, methanol and water;

f) charging the raffinate to a third distillation column and separating it therein into a third higher boiling MTBE product fraction and a third lower boiling aqueous isobutylene fraction;

g) charging the third lower boiling aqueous isobutylene fraction to a decantation zone and separating it therein into an isobutylene chase and water;

h) continuously charging the isobutylene chase and methanol to an isobutylene conversion reactor containing a solid resin etherification catalyst and reacting the isobutylene with methanol therein to form said isobutylene conversion product comprising methyl tertiary butyl ether, unreacted methanol;

i) charging the second higher boiling methanol distillation fraction from the second distillation column and the extract from the methanol solvent extraction tower to a fourth distillation column and separating them therein into a fourth lower boiling MTBE fraction and a fourth higher boiling aqueous methanol fraction;

j) recycling the fourth lower boiling MTBE fraction to the methanol solvent extraction tower; and k) separating methanol from the water in the fourth aqueous methanol fraction and recycling the separated methanol to the etherification reactor.

4. A method as in claim 3 wherein the methanol, the lower boiling isobutylene fraction from the reactive distillation column, and the first lower boiling tertiary butyl alcohol fraction are charged to the methyl tertiary butyl ether etherification reactor in the molar ratio of about 1.1 to about 3.0 moles of methanol per combined mole of tertiary butyl alcohol and isobutylene in the lower boiling isobutylene fraction and the lower boiling tertiary butyl alcohol fraction.

5. A method as in claim 3 wherein the etherification catalysts in the etherification reactor and in the isobutylene conversion reactor are solid resin divinyl benzene cross-linked sulfonated polystyrene catalysts.

6. A method as in claim 3 wherein the methanol is reacted with the tertiary butyl alcohol and isobutylene in the etherification reactor under conversion conditions including a temperature of about 80° C. to about 120° C. and a pressure of about 30 to 500 psia at a flow rate of about 0.5 to 20 volumes of feed mixture per volume of etherification catalyst per hour, and     wherein isobutylene is reacted with methanol in the isobutylene conversion reactor under reaction conditions including a temperature of about 35° to about 130° C., a pressure of about 50 to 500 psia and a flow rate of about 0.5 to about 4 volumes of isobutylene per volume of catalyst per hour.

7. A method as in claim 3 wherein the etherification reaction product is distilled in the second distillation column under distillation conditions including a liquid reflux temperature of about 40° to about 80° C., a reflux ratio of about 1.0 to about 1.5, a reboiler temperature of about 95° to about 105° C., and a pressure of about 15 to about 60 psia.

8. A method as in claim 3 wherein the distillation conditions are selected to provide a lower boiling distillation fraction comprising about 70 to 80 wt. % of methyl tertiary butyl ether, about 10 to 20 wt. % of methanol, about 5 to 15 wt. % of isobutylene and about 0.05 to about 2 wt. % of water.

* * * * *